(12) United States Patent
Hansen et al.

(10) Patent No.: US 9,423,322 B2
(45) Date of Patent: Aug. 23, 2016

(54) METHODS AND COMPOSITIONS FOR HEMATOXYLIN AND EOSIN STAINING

(71) Applicant: Leica Biosystems Richmond, Inc., Richmond, IL (US)

(72) Inventors: Stanley E. Hansen, McHenry, IL (US); Russell Myers, Richmond, IL (US); Ronald Paul, Clancy, MT (US); Audra Rasmussen, Kenosha, WI (US); Kate Taylor, Melbourne (AU)

(73) Assignee: Leica Biosystems Richmond, Inc., Richmond, IL (US)

( * ) Notice: Subject to any disclaimer, the term of this patent is extended or adjusted under 35 U.S.C. 154(b) by 0 days.

(21) Appl. No.: 14/268,274

(22) Filed: May 2, 2014

(65) Prior Publication Data

US 2014/0242634 A1    Aug. 28, 2014

Related U.S. Application Data

(62) Division of application No. 13/750,686, filed on Jan. 25, 2013, now abandoned.

(60) Provisional application No. 61/591,181, filed on Jan. 26, 2012.

(51) Int. Cl.
   *G01N 1/30* (2006.01)
   *G01N 33/48* (2006.01)
   *G01N 33/68* (2006.01)

(52) U.S. Cl.
   CPC ............... *G01N 1/30* (2013.01); *G01N 33/6839* (2013.01); *G01N 2001/302* (2013.01)

(58) Field of Classification Search
   None
   See application file for complete search history.

(56) References Cited

U.S. PATENT DOCUMENTS

| | | | |
|---|---|---|---|
| 4,714,675 A | 12/1987 | Miyashita et al. |
| 5,295,998 A | 3/1994 | Merritello et al. |
| 5,296,090 A | 3/1994 | Solares et al. |
| 5,318,795 A | 6/1994 | Stokes et al. |
| 6,348,325 B1 | 2/2002 | Zahniser et al. |
| 6,544,798 B1 | 4/2003 | Christensen et al. |
| 6,593,102 B2 | 7/2003 | Zahniser et al. |
| 6,735,531 B2 | 5/2004 | Rhett et al. |
| 6,819,787 B2 | 11/2004 | Stone et al. |
| 7,202,041 B2 | 4/2007 | Kamei et al. |
| 7,303,725 B2 | 12/2007 | Reinhardt et al. |
| 7,410,753 B2 | 8/2008 | Hopkins et al. |
| 7,468,161 B2 | 12/2008 | Reinhardt et al. |
| 7,875,245 B2 | 1/2011 | Favuzzi et al. |
| 8,048,373 B2 | 11/2011 | Reinhardt et al. |
| 8,551,731 B2 | 10/2013 | Kosmeder et al. |
| 2004/0014222 A1* | 1/2004 | Towne ............... C12Q 1/6841 436/17 |
| 2004/0219069 A1 | 11/2004 | Kalra et al. |
| 2008/0038836 A1 | 2/2008 | Reinhardt et al. |
| 2008/0227143 A1 | 9/2008 | Kosmeder et al. |
| 2009/0246824 A1 | 10/2009 | Wiederhold et al. |
| 2013/0203109 A1 | 8/2013 | Hansen et al. |
| 2014/0287429 A1 | 9/2014 | Kasamatsu |

FOREIGN PATENT DOCUMENTS

| | | |
|---|---|---|
| EP | 2239554 A1 | 10/2010 |
| JP | S58-179499 A | 10/1983 |
| JP | 2004-514886 A | 5/2004 |
| JP | 2010-521678 A | 6/2010 |
| JP | 4512492 B2 | 7/2010 |
| WO | 2004057308 A1 | 7/2004 |
| WO | 2007/029437 A1 | 3/2007 |
| WO | 2008/112993 A1 | 9/2008 |
| WO | 2009148885 A2 | 12/2009 |
| WO | 2011096468 A1 | 8/2011 |
| WO | WO 2011157678 A1 * | 12/2011 |
| WO | 2013112891 A1 | 8/2013 |

OTHER PUBLICATIONS

Brittain, "Encyclopedia of Pharmaceutical Technology", 3rd Edition, 2007, pp. 385-388, Informa Heathcare, New York, J. Swarbrick (Editor), vol. 1.
Clark, "Effects of Additives on Alum Hematoxylin Staining Solutions", Stain Technology, 1975, pp. 115-118, vol. 50, No. 2.
Graham, "A Quick-Mixed Aluminum Hematoxylin Stain", Biotechnic & Histochemistry, Jan 1, 1991, pp. 279-281, vol. 66, No. 6, Williams & Wilkins, Baltimore, MD, US.
International Preliminary Report on Patentability (Chapter I) for PCT/US2013/023226 issued Aug. 7, 2014.
International Search Report and Written Opinion for PCT/US2013/023226 dated Mar. 27, 2013.
Wang et al., "Effect of PH Value Changes in Ehrlich Haematoxylin Staining Solution on the Straining of Tissue Slices", Med & Pharmaceutical Journal China PLA, Jun. 30, 2011, pp. 24-25, vol. 23, No. 3.
Wang et al., "Effect of PH Value Changes in Ehrlich Haematoxylin Staining Solution on the Straining of Tissue Slices", Med & Pharmaceutical Journal China PLA, Jun. 30, 2011, pp. 24-25, vol. 23, No. 3 with complete English translation.

* cited by examiner

*Primary Examiner* — Renee Claytor
*Assistant Examiner* — Michelle F Paguio Frising
(74) *Attorney, Agent, or Firm* — Thompson Coburn LLP

(57) ABSTRACT

The present invention provide for solutions of a defined composition useful in a staining protocol, such as a hematoxylin and eosin staining protocol, when used at certain points of the staining protocol. The formulations of these defined solutions are such that carry-over of the solutions will not negatively impact, or preferably, will stabilize or favorably modify staining reagent solutions coming in contact with the solutions. In certain embodiments of the invention, solutions are buffered to maintain a specific pH that when carried-over—such as carried-over into hematoxylin—will not significantly influence the pH of the next staining reagent.

14 Claims, 4 Drawing Sheets

METHODS AND COMPOSITIONS FOR HEMATOXYLIN AND EOSIN STAINING

CROSS-REFERENCE TO RELATED APPLICATIONS

This application is a Divisional application of U.S. patent application Ser. No. 13/750,686, filed Jan. 25, 2013, which claims the benefit of U.S. Provisional Patent Application No. 61/591,181 filed Jan. 26, 2012, both of which are incorporated herein by reference in their entireties.

BACKGROUND

The hematoxylin and eosin ("H and E") staining technique is the most commonly used histological technique for the visualization of pathology in tissue specimens. A typical H and E staining system is composed of solutions comprising aluminum based hematoxylin, eosin, a differentiating solution, and a bluing agent. Hematoxylin is a natural dye that when complexed with aluminum ions produces a positively charged molecule that binds to deoxyribonucleic acid to produce a purple coloration of cell nuclei. Differentiation solutions typically are lightly acidic solutions that sharpen the contrast of the stained slide by removing excessive background staining from the tissue and slide. Bluing agents are solutions of a basic pH that when applied to stained specimens modify the structure of the bound hematoxylin to produce a vibrant blue/purple coloration. Eosin is a negatively charged dye that binds to positively charged proteins within the cytoplasm and connective tissue to produce a pink/orange coloration that contrasts with the blue/purple coloration of the nuclei.

H and E staining is most commonly performed in a "batch" format wherein automated stainers typically contain a series of staining reagent containers and utilize a robotic arm for the sequential movement of slides/racks from one container to another. Typically, a rack or holder is capable of carrying 20 to 30 slides although some staining instruments incorporate racks that hold fewer or greater numbers of slides per rack and in the case of at least one stainer, multiple racks may be places into a staining vessel simultaneously. Software controlling an automated stainer allows the operator to program the duration of each of the steps as well as the sequence of the steps. While the batch format of staining is simple, economical, and relatively rapid, there are drawbacks with the technique.

The movement of racks carrying slides from one container to the next results in the carry-over of staining reagents or water. Carry-over occurs due to the adherence of staining reagents or water to the slides, samples, the slide rack, etc. Carry-over is undesirable because it may affect the functionality of the downstream staining reagents in several ways. Carry-over dilutes the concentration of the dyes or functional reagents within a solution. Carry-over and dilution can also affect the functionality of the staining reagent by changing the characteristics of the solvent and thus affecting such parameters such as pH and ionic strength of the solvent. Finally, carry-over may introduce contaminants to the staining reagent. Acting through these mechanisms, carry-over negatively impacts the performance, functionality, stability, predictability, and capacity of the staining system. Although a single instance of carry-over may result in such negative impacts, the negative impacts of carry-over are especially problematic over the course of multiple staining runs as the negative impacts build or are amplified as the result of the cumulative effects of repeated carry-over.

Because of the negative effects of carry-over, the capacity or useful life of reagents in current staining systems is highly unpredictable. Reagents are often changed after a predetermined amount of use based on past experience or changed once they start to exhibit signs of or reach the point of failure. Therefore, solutions in current systems are often changed at different rates, i.e., at different times. This adds complexity and inefficiency as staining is continually stopped to change just one or less than all of the solutions. On the other hand, if all of the solutions are changed at once, some of them are discarded while still having useful capacity to process additional slides, and thus money is wasted.

Typical attempts to address the negative consequences of carry-over have involved replacing staining reagents with fresh solutions, either on a frequent regular basis or even for each individual sample. For example as described in U.S. Pat. Nos. 7,468,161 and 8,048,373. In addition, there have been improvements in individual reagent chemistries (hematoxylin, eosin, differentiator and bluing buffer) that may delayed some of the effects of carryover. In at least one case, there has been an attempt to eliminate the effects of carryover due to the mechanical design of the instrument (Dako CoverStainer). However, unpredictability and loss of staining effectiveness due to carryover still remains a major unresolved problem.

SUMMARY OF THE INVENTION

Certain embodiments of the present invention provide for solutions of a defined composition useful in a staining protocol when used at certain points of the staining protocol. The formulations of these solutions are such that carry-over of the solutions will not negatively impact, or preferably, will stabilize or favorably modify staining reagent solutions coming in contact with solutions defined herein. In certain embodiments of the invention, solutions are buffered to maintain a specific pH that when carried-over—such as carried-over into hematoxylin—will not significantly influence the pH of the next staining reagent.

Certain embodiments of the invention are drawn to methods of reducing the undesirable impact of solution carry-over in an H and E staining system. In certain embodiments, defined solutions are used at various steps of the staining protocol, such as before certain staining reagent steps, to reduce the undesirable impact of carry-over.

In particular, certain embodiments of the invention are drawn to a pH buffered solution comprising an organic acid and a polyhydroxy alcohol. In certain embodiments, the pH buffered solution has a pH buffering range that comprises from about pH 2.0 to about pH 5.0. In certain embodiments, the pH buffered solution has a pH buffering range of from about pH 1.0 to about pH 7.0, or from about pH 1.0 to about pH 6.0, or from about pH 1.0 to about pH 5.0., or from about pH 2.0 to about pH 7.0, or from about pH 2.0 to about pH 6.0. Preferably, such pH buffered solution has a pH buffering range of from about pH 2.0 to about pH 5.0. The pH buffered solution may comprise from about 5% to about 30% (v/v) of a polyhydroxy alcohol selected from the group consisting of ethylene glycol, propylene glycol, glycerin, and polyethylene glycol and may comprise from 10 mM to about 100 mM of an organic acid selected from the group consisting of malic acid, citric acid, maleic acid, acetic acid, and tartaric acid. In certain embodiments, the pH buffered solution may also comprise an antimicrobial agent that is effective over at least a pH range of from about pH 2.0 to about pH 5.0.

Certain embodiments of the invention are drawn to a solution with a pH of from about pH 2.0 to about pH 5.0 comprising aluminum salts and from about 5% to about 30% (v/v)

of a polyhydroxy alcohol selected from the group consisting of ethylene glycol, propylene glycol, glycerin, and polyethylene glycol.

Certain embodiments of the invention are also drawn to a method of staining a tissue specimen with hematoxylin, the method comprising the steps of (i) contacting the specimen to a defined solution of the invention and (ii) transferring the specimen to a hematoxylin staining solution. Additionally, the method may comprise the steps of rinsing the specimen with water and then contacting the specimen with the buffered solution.

Certain embodiments of the invention are drawn to a kit for performing hematoxylin and eosin staining, the kit comprising a defined solution of the invention and at least one hematoxylin and eosin staining reagent selected from the group consisting of a hematoxylin solution, an eosin solution, a differentiating solution, and a bluing agent solution.

DETAILED DESCRIPTION

Figure 1:
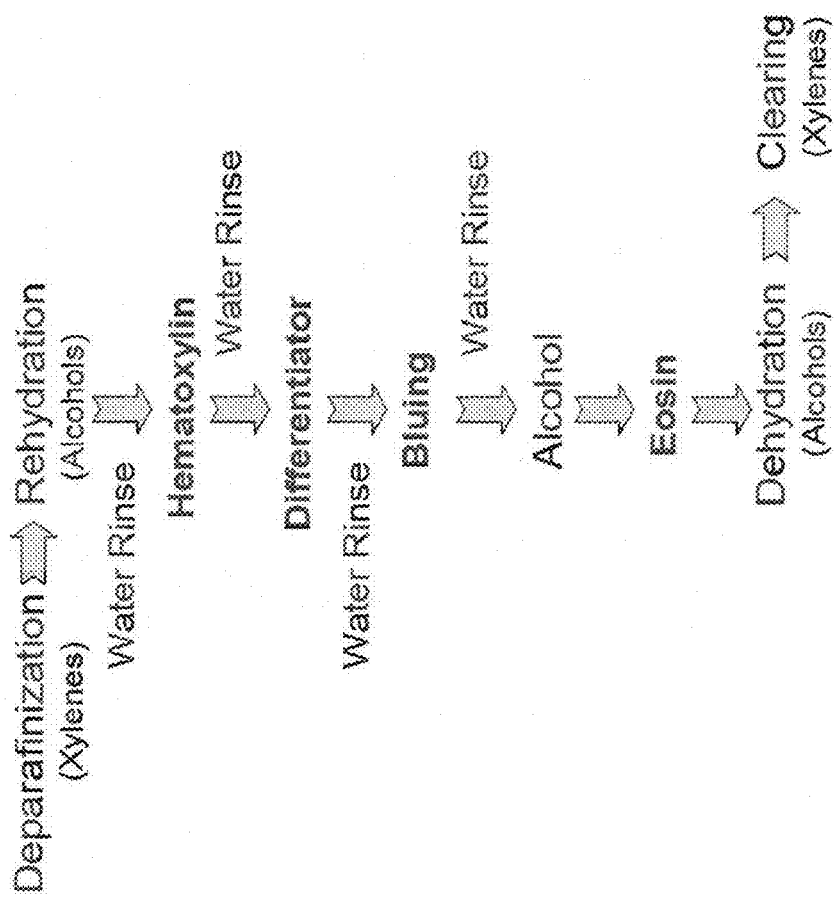
FIG. 1 shows the steps of a typical hematoxylin and eosin staining protocol.

Headings are provided herein solely for ease of reading and should not be interpreted as limiting.

I. Definitions

The following definitions are provided to better define the present invention and to guide those of ordinary skill in the art in the practice of the invention. Unless otherwise noted, terms are to be understood according to conventional usage by those of ordinary skill in the relevant art.

Where a term is provided in the singular, the inventors also contemplate aspects of the invention described by the plural of that term unless otherwise indicated.

As used herein, a "staining reagent" refers to any reagent used in a histological staining protocol. Where it is necessary to understand the invention by specifically referring to "a reagent that is a stain" versus "a reagent in the staining process that is not a stain," such a distinction is explicitly made.

As used herein, a "working strength" or "ready-to-use" solution is a solution wherein the components in the solution are at the desired concentration for use in the methods of the present invention. "Ready-to-use" may also imply that the solution does not require any additional manipulation on the part of the end user such as filtration, skimming, and/or mixing.

As used herein, "xylene substitutes" which are in widespread use include two classes: terpenes and aliphatic solvents. Representative examples of terpenes include limonene and turpentine.

Typically, tap water is most economical to use as a rinse step in high capacity H and E staining protocols. Thus, as used herein, the term "water" refers to tap water, but also covers distilled or deionized water or aqueous solutions used to treat or rinse specimens in an H and E staining system.

II. Overview

It has been discovered that the undesirable impact of solution carry-over in H and E staining protocols can be ameliorated by the use of certain defined solutions in-between certain steps of the protocol. It is believed that the adoption of these solutions and methods will increase the capacity for staining samples (such as those mounted on slides or slides held in racks, etc.), which may translate into cost-savings for end-user. Other expected benefits include an improved user experience due to increased ease of use, more predictability in reagent performance, and decreased effort and labor. In addition, it is believed that the solutions and methods disclosed herein will save time and increase efficiency as the downtime necessary for changing reagents will be reduced. Consistency (quality) of results will also be enhanced as variability introduced through carry-over and dilution of reagents will be minimized and the predictability of reagent performance will also be improved.

III. Hematoxylin and Eosin ("H and E") Staining

H and E staining is a widely used staining method for histological purposes. One of skill in the art will recognize that many variations and protocols for H and E staining have been developed and where the present invention is applicable, the present invention is not limited to any specific variation, protocol, system, or the like. A typical H and E staining system may be defined as composed of four core staining reagents: hematoxylin, differentiator, bluing reagent, and eosin, as well as the necessary rinses and solvents utilized for deparaffinization, rehydration, dehydration, and clearing.

A typical, representative H and E staining protocol comprises the steps of (i) deparaffinization (using xylenes or xylene substitutes), (ii) rehydration (using alcohols), (iii) water rinse, (iv) hematoxylin, (v) water rinse, (vi) differentiator, (vii) water rinse, (viii) bluing, (ix) water rinse, (x) alcohol, (xi) eosin, (xii) dehydration (using alcohols), and (xiii) clearing (using xylenes or xylene substitutes) (Sheenan, D. C. and Hrapchak, B. B.: *Theory and Practice of Histotechnology* 2$^{nd}$ ed. Columbus, Ohio, Battelle Press, 1980) (FIG. 1). In certain embodiments of the invention, a step of using a defined solution immediately precedes a step in the H and E staining protocol. The composition of the solution is dictated by the staining reagent that the solution is designed to protect from carry-over. In certain preferred embodiments, a step of using a defined solution of the invention immediately precedes a core staining reagent step.

In certain embodiments of the invention, a step of using a defined solution immediately precedes the hematoxylin step. In certain embodiments of the invention, a step of using a defined solution immediately precedes the differentiator step. In certain embodiments of the invention, a step of using a defined solution immediately precedes the bluing reagent step. In certain embodiments of the invention, a step of using a defined solution immediately precedes the eosin step.

Figure 2:
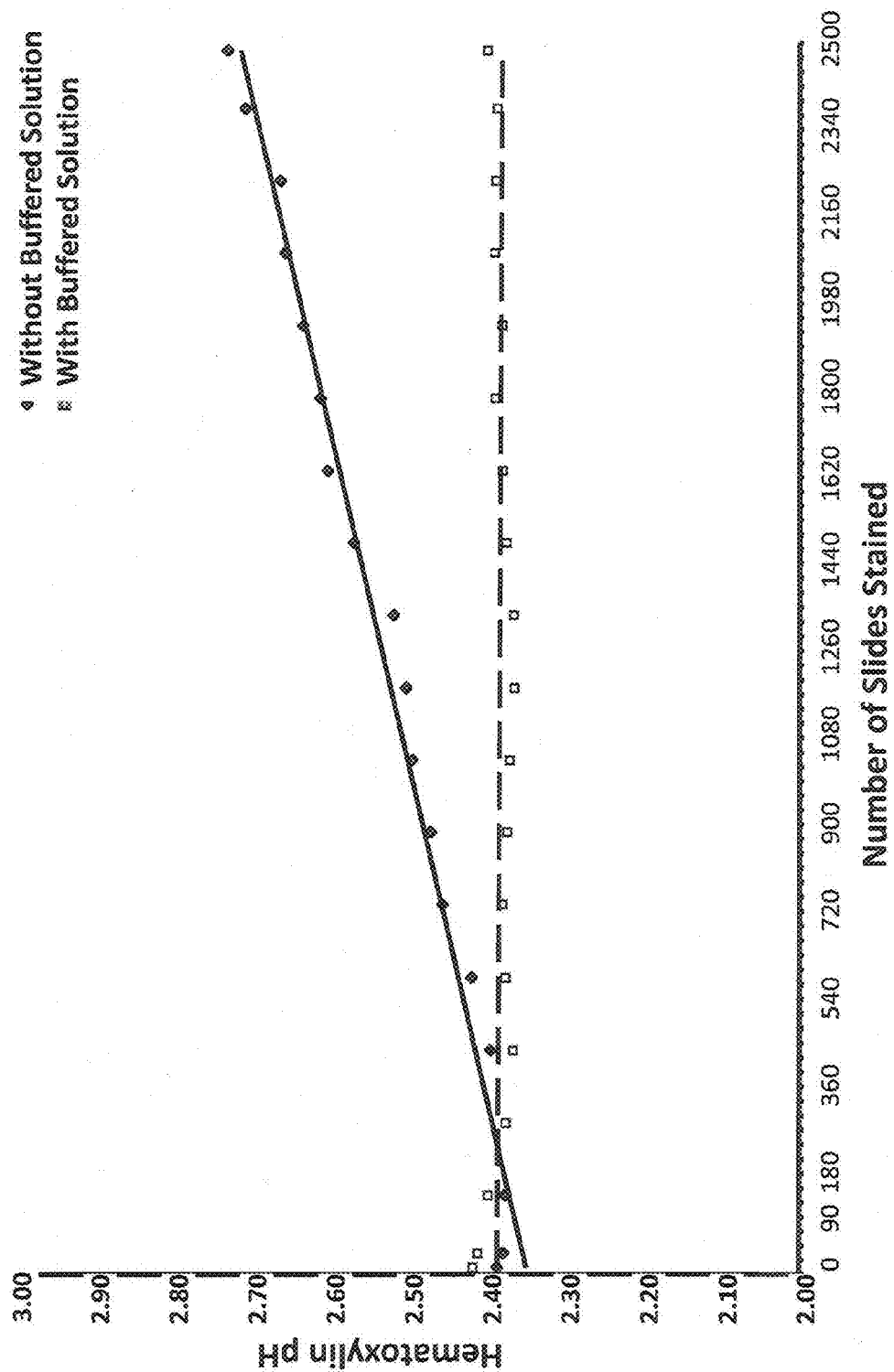
FIG. 2 shows changes in the pH of a hematoxylin solution during the sequential staining of 2,500 slides with specimens. Staining of multiple slides results in an increase in the pH of the hematoxylin solution (solid line). Placement of a buffered solution of defined composition prior to the hematoxylin prevents an increase in pH of the hematoxylin (dashed line).
Figure 3:
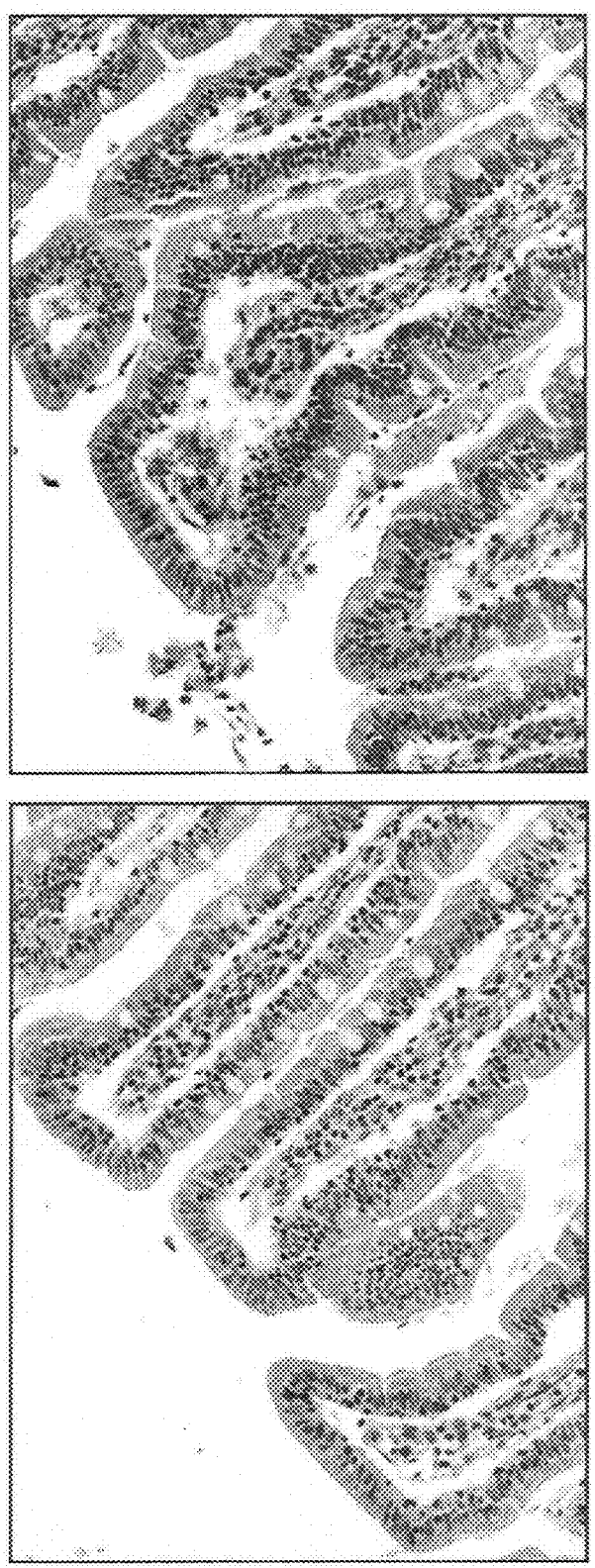
FIG. 3 shows changes in the quality of hematoxylin staining of specimens following the sequential staining of 2,500 slides. Increased cytoplasmic background staining and loss of detail is present in the 2,500$^{th}$ slide as compared to the first slide.
Figure 4:
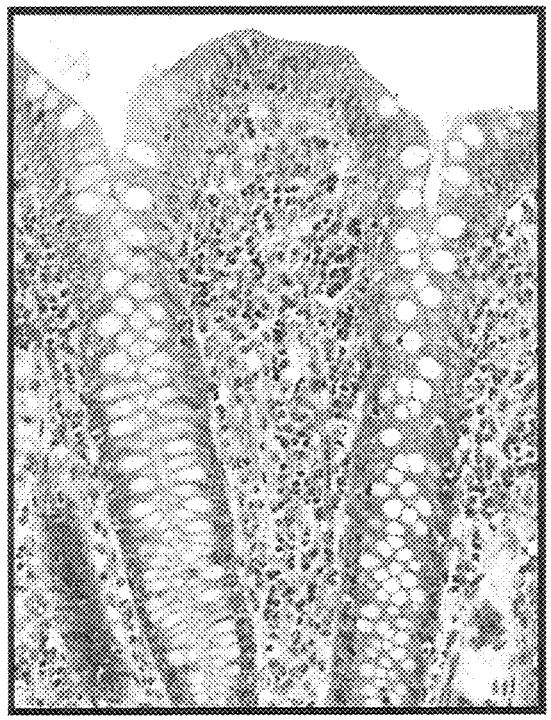
FIG. 4 shows consistent hematoxylin staining observed in the first and 2,500$^{th}$ sequentially stained specimens. Slides were stained with a protocol using a buffered solution of defined composition of the invention between the tap water rinse and the hematoxylin solution.
Figure 4:
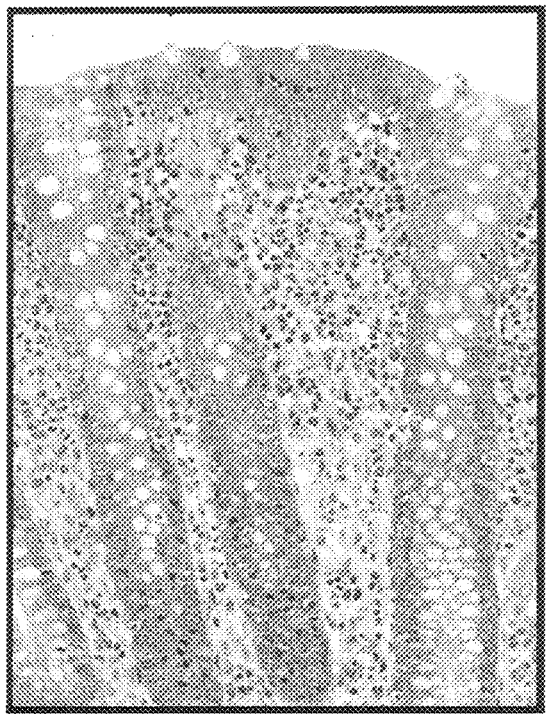

In certain embodiments of the invention, a solution with a defined composition is placed between a water rinse step and the hematoxylin solution. In certain embodiments, the rinse water is tap water. In this position, the defined solution mitigates several adverse effects of the water on the hematoxylin solution. By reducing the actual volume of water that is carried over from the rinse step into the hematoxylin, the volume of components (for example, ions, chlorine, etc.) within the water (and especially such as found in tap water) that may affect the staining quality or staining capacity of the hematoxylin is reduced. The addition of a buffer to the solution reduces the capacity of the water to increase the pH of the hematoxylin (FIG. 2). This is advantageous because an increase in the pH of the hematoxylin results in background staining of tissues and loss of staining detail (FIGS. 3 and 4).

In addition to mitigating the adverse effects of carry-over, the defined solution may be formulated to enhance the stability of a hematoxylin exposed to carry-over of the solution. The addition of a polyhydroxy alcohol to the solution to be carried over to the hematoxylin can reduce the likelihood of precipitation of the hematoxylin and can provide value to the user as filtration of the hematoxylin will not be necessary.

It is understood that a step of "using" a solution means exposing a sample—for example a tissue specimen mounted on a slide—to a solution. A sample may be exposed to a solution, for example, by dunking or immersing it in the solution. A sample may be exposed to a solution, for example, by passing the solution over the sample, such as by passing a solution over a slide holding a sample. A sample may be exposed to a solution, for example, by dropping or spraying the solution onto a sample. One of skill in the art will recognize that there may be various alternative methods of exposing a sample to a solution during the staining process, and that the method and solutions of the present invention are not limited to any particular method of exposing a sample to solution.

IV. Defined Solutions for Mitigating the Effects of Carry-Over

One aspect of the present invention provides for solutions of defined composition for mitigating the effects of water or staining reagent carry-over in a histological staining protocol.

In certain embodiments, the defined solution is a buffered solution comprising an acid, the buffered solution being capable of buffering from between about pH 2.0 to about pH 5.0. In certain embodiments, the acid has a pKa of from about 2.0 to about 5.0. In certain embodiments, the concentration of the acid in the solution is from about 10 mM to about 100 mM. In certain embodiments, the concentration of the acid in the solution is from about 20 mM to about 100 mM. In certain embodiments, the concentration of the acid in the solution is from about 10 mM to about 50 mM or from about 20 mM to about 50 mM. In certain embodiments, the acid is an organic acid. Representative examples of useful organic acids include, but are not limited to, malic acid, citric acid, fumaric acid, tartaric acid, maleic acid, and acetic acid. In certain embodiments, the buffered solution comprises a polyhydroxy alcohol at a concentration of from about 5% to about 30% (v/v). Representative examples of polyhydroxy alcohols include, but are not limited to, ethylene glycol, polyethylene glycol, propylene glycol, and glycerin. In certain embodiments, the solution comprises both an acid and a polyhydroxy alcohol in the amounts and as defined herein. In a certain specific embodiment, the buffered solution is a solution comprising 20 mM tartaric acid and 15% (v/v) ethylene glycol and the solution pH is adjusted to a pH of 3.3. One of skill in the art will understand that there are numerous reagents that can be used to adjust pH. For example, sodium hydroxide (NaOH), potassium hydroxide (KOH), or other hydroxide based compounds, and tartaric acid and its conjugate base. In one embodiment, the pH is adjusted with sodium hydroxide (NaOH).

In certain embodiments, the defined solution is an unbuffered solution with a pH of from about pH 2.0 to about pH 5.0 comprising aluminum salts. Representative examples of aluminum salts include, but are not limited to, aluminum ammonium sulfate [$AlNH_4(SO_4)_2$], aluminum sulfate [$Al_2(SO_4)_3$], and aluminum potassium sulfate $AlK(SO_4)_2$. In certain embodiments, the unbuffered aluminum salt solution also comprises a polyhydroxy alcohol as described herein at a concentration of from about 15% to about 30% (v/v).

In certain embodiments, the defined solution is a slightly modified or non-modified formulation of the staining reagent used as the differentiator. In certain embodiments, the slightly modified or non-modified formulation of the staining reagent used as the differentiator is a solution buffered with any acid, where the acid has a pKa of from about 2.5 to about 4.0 and is capable of buffering between a pH of from about pH 1.5 to about pH 5.0. In certain embodiments, the acid is an organic acid. Representative examples of useful organic acids include, but are not limited to, malic acid, citric acid, fumaric acid, maleic acid, acetic acid, and tartaric acid.

In embodiments encompassing any of the solutions of the invention, or solutions useful in practicing the methods of the invention, an antimicrobial agent may be added to inhibit microbial growth. In certain embodiments, the antimicrobial agent is one that is effective over at least a pH range of from about pH 2.0 to about pH 5.0. Representative examples of microbial agents include sodium azide, PROCLIN 300®, PROCLIN 150®, PROCLIN 200®, and PROCLIN 950®. For example, in one embodiment, the solution contains from about 0.03% to about 0.04% (v/v) PROCLIN 300® (Sigma Aldrich, St. Louis, Mo.) to inhibit microbial growth. It is to be understood that example product or trade names known to those of ordinary skill in the art are provided for illustrative purposes only and are not meant to be limiting of the broader genus of reagents described.

It is contemplated that the defined solutions, such as the buffered solutions, of the invention will be provided as a working strength or ready-to-use solution for H and E staining protocols. However, it is also contemplated that concentrated solutions of two or more components may be prepared wherein a user may add water and/or other components (such as an antimicrobial) to the defined solution to prepare a working strength or ready-to-use solution with the formulations described herein. Thus, the present invention is also drawn to concentrated solutions that can be used to prepare the defined solutions of the invention. Given the amounts of components in the defined solutions provided, it is within the skill of one of ordinary skill in the art to determine what the amounts of components in a concentrated solution must be to provide for a working strength or ready-to-use solution. For example, if the concentrate is to be diluted 1:1 with water, then the concentration of an acid, polyhydroxy alcohol, etc., would be twice what the desired final concentration would be.

V. Methods of Mitigating the Effects of Carry-Over

One aspect of the present invention provides for methods of mitigating the effects of water or staining reagent carry-over in a histological staining protocol. In general, such methods utilize a defined solution as a step in the staining process between two staining reagent steps or between a water rinse step and a staining reagent step.

In staining protocols where samples are contacted with staining reagents by immersing the samples in the staining reagents, the samples may also be immersed in the defined solution. In staining protocols where samples are contacted with staining reagents in a manner other than immersion, the samples may be contacted with the defined solution in a likewise manner. It is understood, however, that the manner in which the samples are contacted with the staining reagents does not limit the manner in which the sample may be contacted with the defined solution within the same staining protocol.

In an H and E staining system, the detrimental effects of carry-over are greatest on the hematoxylin and differentiator solutions, but may affect all stains/reagents in a staining system. Hematoxylin and the differentiator follow water rinses in a typical H and E staining schedule. The performance of these two solutions is highly dependent upon pH and the introduction of water to these solutions results in an increase in pH. One effect of increased pH on these solutions is an increase in the background staining of hematoxylin. In certain embodiments, a sample is contacted with a defined solution immediately before being contacted with a hematoxylin staining solution. In certain embodiments, the sample is contacted with a defined solution immediately after being rinsed in water and immediately before being contacted with a hematoxylin staining solution. In certain embodiments, the pH of the hematoxylin solution will increase less than 0.30 pH units when exposed to a buffered solution carried over from prior immersion of the specimen in the buffered solution. In certain embodiments, the pH of the hematoxylin solution will increase less than 0.20 pH units when exposed to a buffered solution carried over from prior immersion of the specimen in the buffered solution. It is understood that not only will the pH of the hematoxylin solution increase less than 0.30 pH units, or less than 0.2 pH units, when exposed to a buffered solution carried over from prior immersion of the specimen in the buffered solution when carrying out the steps of the method once, but that a particular advantage of the inventions is that the pH of hematoxylin solution will not increase after repeated exposures to carryover of the buffered solution.

In certain embodiments, a sample is contacted with a defined solution immediately before being contacted with a differentiator solution. In certain embodiments, the sample is contacted with a defined solution immediately after being rinsed with water and immediately before being contacted with a differentiator solution.

Use of the described methods may allow for up to 2,000 standard specimen slides to be processed under standard H and E staining procedures before new reagents are substituted. In certain embodiments, use of the methods may allow for up to 2,700 slides to be processed before new reagents are substituted. Further, in certain embodiments, use of the methods may allow for up to 3,000 slides to be processed before new reagents are substituted. It is understood by those of skill in the art that the capacity to process a certain number of specimen slides refers to the capacity to process such a number without observing an adverse effect on staining that would be unacceptable for the purpose for which the slides are being stained. It is further contemplated that use of the reagents and methods of the invention used in combination with mechanical methods that reduce, but do not completely eliminate carry-over, will also significantly enhance the number of slides that may be stained using a given set of reagents.

Methods of the invention may also include the step of diluting a concentrated solution, such as diluting with water, to a final working strength or ready-to-use defined solution. Methods of the invention may also include the step of adding a component, such as an antimicrobial, to prepare a ready-to-use defined solution. This step would be performed before using the defined solution in an H and E staining protocol.

VI. Kits and Methods of Use

One aspect of the present invention is drawn to kits for performing H and E staining. Such kits comprise at least a defined solution that mitigates the effects of solution carry-over. Useful defined solutions are described in detail in this application and include buffered and unbuffered solutions. Representative kits of the invention may also comprise one or more staining reagents or other components used for H and E staining. Examples of staining reagents used for H and E staining include hematoxylin solution, eosin solution, a differentiating solution, and a bluing agent solution. Examples of other components used for H and E staining include xylenes, xylene substitutes, and alcohols. In certain embodiments, the kit comprises at least the five reagents: (1) hematoxylin solution, (2) eosin solution, (3) a differentiating solution, (4) a bluing agent solution, and (5) a defined solution that mitigates the effects of solution carry-over.

Another aspect of the invention is drawn to methods of using a kit for performing H and E staining. The procedure for performing the H and E staining includes using a defined solution that mitigates the effects of carry-over as described in detail in this application. The use of a kit provides numerous benefits. Current H and E staining procedures and reagents are subject to the negative effects of solution carry-over, often necessitating that the solutions be changed at different rates. The inclusion of a defined solution that mitigates the effects of solution carry-over in a kit provides for a predictable lifespan of all the kit reagents that is consistent, such that the kit reagents require changing at the same time. For example, use of the kit reagents may allow for up to 2,000 standard specimen slides to be processed using standard H and E staining procedures before new reagents are substituted. Or use of the kit may allow for up to 2,700 slides to be processed before new reagents are substituted. Or use of the kit may allow for up to 3,000 slides to be processed before new reagents are substituted.

EXAMPLES

The following disclosed embodiments are merely representative of the invention which may be embodied in various forms. Thus, specific structural, functional, and procedural details disclosed in the following examples are not to be interpreted as limiting.

Example 1

All staining was performed on either the LEICA® ST-5010 AUTOSTAINER™ or the LEICA® ST-5020 MULTI-STAINER™ utilizing a standard H and E program as outlined in FIG. 1 and Table 1. The goal of the depletion study was to evaluate the chemical and functional (staining) changes that occur during sequential staining of numerous slides. In a typical depletion study (Table 1) the hematoxylin, differentiator, bluing agent and eosin were not changed during the entire depletion study while all of the other components (alcohols and xylenes) were rotated or changed at 300 slide intervals. Staining of control tissue specimens on multi-tissue control slides (functional staining) and determination of the pH of the hematoxylin were performed at 150 slide intervals. A standard depletion study incorporated a total of 2,700 slides (90 30-slide racks).

Other staining runs incorporated an additional buffered reagent of defined composition places between the tap-water rinse and the hematoxylin step (Table 2). This solution was designed to mitigate the effects of carry-over of the tap-water into the hematoxylin. This solution like the hematoxylin, differentiator, bluing agent, and eosin was not changed during the depletion study. As with the study described above, staining of control tissue specimens on multi-tissue control slides (functional staining) and determination of the pH of the hematoxylin were performed at 150 slide intervals.

FIG. 2 demonstrates the increase in pH of the hematoxylin that occurs as slide racks with slides carry over tap-water to the hematoxylin. In contrast, the placement of a buffered reagent of defined composition between the tap water and the hematoxylin displaces the tap-water from the slides prior to movement into the hematoxylin solution. As a result, the pH of the hematoxylin remains stable.

Table 1 shows a standard H and E protocol performed on a LEICA® ST-5010XL™ Automated Stainer.

| Leica Auto Stainer ST5010 XL | | | | | | Withdrawal |
|---|---|---|---|---|---|---|
| Step | Station | Reagent | Time | Exact | Dips | Speed |
| 1 | Oven | | 0:00:00 | NO | 2 | 9 |
| 2 | 1 | Xylene | 0:03:00 | NO | 2 | 9 |
| 3 | 2 | Xylene | 0:03:00 | NO | 2 | 9 |
| 4 | 3 | Xylene | 0:02:00 | NO | 2 | 9 |
| 5 | 4 | 100% Reagent Alcohol | 0:01:00 | NO | 2 | 9 |
| 6 | 5 | 100% Reagent Alcohol | 0:01:00 | NO | 2 | 9 |
| 7 | 6 | 100% Reagent Alcohol | 0:01:00 | NO | 2 | 9 |
| 8 | 7 | 80% Reagent Alcohol | 0:01:00 | NO | 2 | 9 |
| 9 | WSH 1 | Water Wash | 0:01:00 | NO | 2 | 9 |
| 10 | 8 | Hematoxylin | 0:03:00 | YES | 2 | 9 |
| 11 | WSH 5 | Water Wash | 0:03:00 | YES | 2 | 9 |
| 12 | 9 | Differentiator | 0:00:45 | YES | 2 | 9 |
| 13 | WSH 4 | Water Wash | 0:02:00 | YES | 2 | 9 |
| 14 | 10 | Bluing | 0:01:00 | NO | 2 | 9 |
| 15 | WSH 3 | Water Wash | 0:02:00 | YES | 2 | 9 |
| 16 | 11 | 80% Reagent Alcohol | 0:01:00 | NO | 2 | 9 |
| 17 | 12 | Eosin | 0:01:00 | NO | 2 | 9 |
| 18 | 13 | 100% Reagent Alcohol | 0:01:00 | YES | 2 | 9 |
| 19 | 14 | 100% Reagent Alcohol | 0:01:00 | YES | 2 | 9 |
| 20 | 15 | 100% Reagent Alcohol | 0:01:00 | YES | 2 | 9 |
| 21 | 16 | Xylene | 0:01:00 | YES | 2 | 9 |
| 22 | 17 | Xylene | 0:01:00 | NO | 2 | 9 |
| 23 | 18 | Xylene | 0:01:00 | NO | 2 | 9 |
| 24 | EXIT | Xylene | | | | |

Table 2 shows an H and E protocol using a buffered solution of defined composition places between the tap water rinse step and hematoxylin step (Step 10 in Table 2) on a LEICA® ST-5010XL™ Automated Stainer.

| Leica, ST5010 Autostainer XL | | | | | | Withdrawal |
|---|---|---|---|---|---|---|
| Step | Bath-Station | Reagent | Time | Exact | Dips | Speed |
| 1 | LOAD | — | 0:00:00 | NO | 2 | 9 |
| 2 | 1 | Xylene | 0:02:00 | NO | 2 | 9 |
| 3 | 2 | Xylene | 0:02:00 | NO | 2 | 9 |
| 4 | 3 | Xylene | 0:02:00 | NO | 2 | 9 |
| 5 | 4 | 100% Reagent Alcohol | 0:01:00 | NO | 2 | 9 |
| 6 | 5 | 100% Reagent Alcohol | 0:01:00 | NO | 2 | 9 |
| 7 | 6 | 100% Reagent Alcohol | 0:01:00 | NO | 2 | 9 |
| 8 | 7 | 80% Reagent Alcohol | 0:01:00 | NO | 2 | 9 |
| 9 | WSH 1 | Water Wash | 0:01:00 | NO | 2 | 9 |
| 10 | WSH 2 | Buffered Solution | 0:00:30 | YES | 2 | 9 |
| 11 | 8 | ST-Hematoxylin | 0:03:00 | YES | 2 | 9 |
| 12 | WSH 5 | Water Wash | 0:02:00 | YES | 2 | 9 |
| 13 | 9 | ST-Differentiator | 0:00:45 | YES | 2 | 9 |
| 14 | WSH 4 | Water Wash | 0:01:00 | NO | 2 | 9 |
| 15 | 10 | ST-Bluing Reagent | 0:01:00 | YES | 2 | 9 |
| 16 | WSH 3 | Water Wash | 0:01:00 | NO | 2 | 9 |
| 17 | 11 | 80% Reagent Alcohol | 0:01:00 | NO | 2 | 9 |
| 18 | 12 | ST-Eosin | 0:01:00 | YES | 2 | 9 |
| 19 | 13 | 100% Reagent Alcohol | 0:01:00 | YES | 2 | 9 |
| 20 | 14 | 100% Reagent Alcohol | 0:01:00 | YES | 2 | 9 |
| 21 | 15 | 100% Reagent Alcohol | 0:01:00 | YES | 2 | 9 |
| 22 | 16 | Xylene | 0:01:00 | NO | 2 | 9 |
| 23 | 17 | Xylene | 0:01:00 | NO | 2 | 9 |
| 24 | 18 | Xylene | 0:01:00 | NO | 2 | 9 |
| 25 | EXIT | Xylene | | | | |

Table 3 shows a representative example of a buffered solution of defined composition of the invention, such as for use immediately prior to contacting a specimen slide with hematoxylin solution. The pH is adjusted to 3.33 with 2N NaOH.

| Raw Material | 1 liter formula |
|---|---|
| Deionized Water | 850.00 ml |
| Tartaric Acid | 3.10 g |
| Ethylene Glycol | 150.00 ml |
| PROCLIN 300® | 0.30 ml |
| Sodium Hydroxide (1M solution) | 14.00 ml |

What is claimed is:

1. A method of staining a tissue specimen with hematoxylin, the method comprising the steps of (i) contacting the specimen with a pH buffered solution comprising an organic acid and a polyhydroxy alcohol, wherein the pH buffered solution has a pH buffering range that comprises from about pH 2.0 to about pH 5.0 and (ii) transferring the specimen to a hematoxylin staining solution wherein the step of contacting the specimen with the pH buffered solution immediately precedes the step of transferring the specimen to the hematoxylin staining solution.

2. The method of claim 1 further comprising rinsing the specimen with water before contacting the specimen with the pH buffered solution.

3. The method of claim 2 wherein the pH buffered solution maintains a pH of from about pH 2.0 to about pH 5.0 when exposed to water carried over from prior contact of the specimen with water.

4. The method of claim 1 wherein the pH of the hematoxylin staining solution increases less than 0.30 pH units when exposed to pH buffered solution carried over from prior contact of the specimen with the pH buffered solution.

5. The method of claim 1 wherein the hematoxylin solution retains its staining capacity longer without an adverse change in staining characteristics than performing hematoxylin staining without contacting the specimen with the pH buffered solution.

6. The method of claim 1 wherein the method provides the capacity to stain at least about 2,700 standard specimen slides without an adverse change in staining characteristics using standard hematoxylin and eosin staining procedures without changing the staining reagents.

7. The method of claim 1 wherein the pH buffered solution comprises from about 5% to about 30% (v/v) of a polyhydroxy alcohol selected from the group consisting of ethylene glycol, propylene glycol, glycerin, and polyethylene glycol.

8. The method of claim 1 wherein the pH buffered solution comprises from about 5% to about 30% (v/v) of ethylene glycol.

9. The method of claim 1, wherein the organic acid is selected from the group consisting of malic acid, citric acid, maleic acid, acetic acid, and tartaric acid.

10. The method of claim 1, wherein the organic acid is selected from the group consisting of malic acid, citric acid, and tartaric acid.

11. The method of claim 1, wherein the organic acid is tartaric acid.

12. The method of claim 1, wherein the pH buffered solution comprises a concentration of from about 10 mM to about 100 mM of the organic acid.

13. The method of claim 1 wherein the pH buffered solution comprises from about 10 mM to about 100 mM of tartaric acid and from about 5% to about 30% (v/v) of ethylene glycol.

14. The method of claim 1 wherein the pH buffered solution further comprises an antimicrobial agent that is effective over at least pH range of from about pH 2.0 to about pH 5.0.

* * * * *